(12) United States Patent
Guzman

(10) Patent No.: US 9,675,787 B2
(45) Date of Patent: Jun. 13, 2017

(54) ANTISEPTIC APPLICATOR

(75) Inventor: Manuel Guzman, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 710 days.

(21) Appl. No.: 13/427,371

(22) Filed: Mar. 22, 2012

(65) Prior Publication Data
US 2013/0251439 A1    Sep. 26, 2013

(51) Int. Cl.
A61M 35/00    (2006.01)
A61L 2/00     (2006.01)
A61F 13/40    (2006.01)

(52) U.S. Cl.
CPC ......... *A61M 35/003* (2013.01); *A61L 2/0088* (2013.01); *A61M 35/006* (2013.01)

(58) Field of Classification Search
CPC ... A61M 35/00; A61M 35/003; A61M 35/006
USPC ....... 401/132–135, 261, 263, 264, 205, 207, 401/270; 604/2, 3; 215/213, 254
See application file for complete search history.

(56) References Cited

U.S. PATENT DOCUMENTS

| 4,507,111 | A | 3/1985 | Gordon et al. | |
| 5,791,801 | A | 8/1998 | Miller | |
| 6,447,476 | B1 | 9/2002 | Sogaro | |
| 8,801,312 | B2* | 8/2014 | Guzman et al. | 401/134 |
| 8,821,059 | B2* | 9/2014 | Sasaki et al. | 401/263 |
| 2002/0076258 | A1 | 6/2002 | Crosby et al. | |
| 2006/0018701 | A1* | 1/2006 | Mohiuddin | 401/132 |
| 2006/0039742 | A1* | 2/2006 | Cable et al. | 401/134 |
| 2007/0196159 | A1 | 8/2007 | Sogaro | |
| 2007/0276312 | A1 | 11/2007 | Davis et al. | |
| 2008/0245314 | A1 | 10/2008 | Brodowski et al. | |
| 2011/0299911 | A1 | 12/2011 | Sasaki et al. | |
| 2012/0065619 | A1 | 3/2012 | Ahlgrimm | |
| 2013/0108352 | A1* | 5/2013 | Ruiz et al. | 401/132 |
| 2013/0156485 | A1* | 6/2013 | Guzman | 401/133 |
| 2013/0156486 | A1* | 6/2013 | Guzman et al. | 401/134 |

(Continued)

FOREIGN PATENT DOCUMENTS

DE    1 199 106 A1    4/2002

OTHER PUBLICATIONS

International Search Report of PCT/US2013033308 dated Nov. 23, 2015.

(Continued)

*Primary Examiner* — Jennifer C Chiang
*Assistant Examiner* — Bradley Oliver
(74) *Attorney, Agent, or Firm* — Arent Fox LLP

(57) ABSTRACT

An applicator assembly includes a head portion having a proximal end, a distal end, and an interior portion defining a fluid chamber, a container slidably coupled to the head portion, a plug sealing an end of the container, an application member attached to the distal end, and one or more orifices formed through a surface of the plug, wherein the plug is mounted in the interior portion of the head portion and an interior of the container is placed in fluid communication with the application member by way of a fluid conduit that is formed through the plug from the container to the fluid chamber when the container is axially translated toward the head portion to bring the one or more orifices into fluid communication with the container.

23 Claims, 2 Drawing Sheets

(56) References Cited

U.S. PATENT DOCUMENTS

2014/0016981 A1* 1/2014 Levine .......................... 401/134
2014/0051178 A1* 2/2014 Niggel et al. ................. 436/164

OTHER PUBLICATIONS

International Search Report dated Jul. 18, 2013 issued in international application No. PCT/US2013/033308.

* cited by examiner

ANTISEPTIC APPLICATOR

BACKGROUND

Field

The present disclosure relates to an antiseptic applicator and method of use thereof, and more particularly, to a sealing plug antiseptic applicator that requires the application of opposing forces to actuate release of a sealed solution, preferably an antimicrobial solution, from a self-contained reservoir toward a material arranged at a distal end of the applicator for receiving the solution.

Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133.

Conventional antiseptic applicators, as described above, often require special packaging and/or handling during shipping and prior to use. For example, with the puncture type applicators, preventive measures are required to prevent an inadvertent push against either end of the device that may result in the puncturing of the sealed container and the premature discharge of the solution. A user must often use both hands to effectively overcome the preventive measures and activate the applicator for use. In addition, conventional antiseptic applicators often rely on the exertion of pressure on the walls of an applicator, for example, to break a frangible ampoule or squeeze the solution from the container toward an application material. The use of frangible ampoules requires special care to avoid breaking as a result of inadvertent pressure or dropping during shipping or prior to use. Furthermore, the components of a conventional applicator, such as the broken ampoule or the puncture spike, often impede the free flow of the solution from the container. There exists a need in the field for a novel antiseptic applicator that avoids the complications associated with conventional applicators, especially an applicator that will allow for effective one hand actuation and application of a solution without impediments to the free flow of the solution from the container to the application material.

SUMMARY

In accordance with aspects of the present invention, an applicator assembly may include a head portion having a proximal, a distal end, and an interior portion defining a fluid chamber, a container slidably coupled to the body, a plug sealing an end of the container, an application member attached to the distal end, and one or more orifices formed through a surface of the plug, wherein the plug is mounted in the interior portion of the head portion and an interior of the container is placed in fluid communication with the application member by way of a fluid conduit that is formed through the plug from the container to the fluid chamber when the container is axially translated toward the head portion to bring the one or more orifices into fluid communication with the container.

In accordance with another aspect of the present invention, a mechanical stop may be provided to secure the container in a predetermined position until the stop is released prior to actuation of the applicator.

In accordance with other aspects of the present invention, the one or more orifices provide fluid communication form an exterior portion of the plug into a hollow body portion of the plug when the container translates toward the distal end of the head portion.

In accordance with another aspect of the present invention, the applicator assembly may further include a separable closing member sealing the other end of the container from the end having the plug.

In accordance with another aspect of the present invention, the applicator assembly may further include a stop ring provided on a surface of the plug and disposed between the one or more orifices and the distal end of the head portion.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
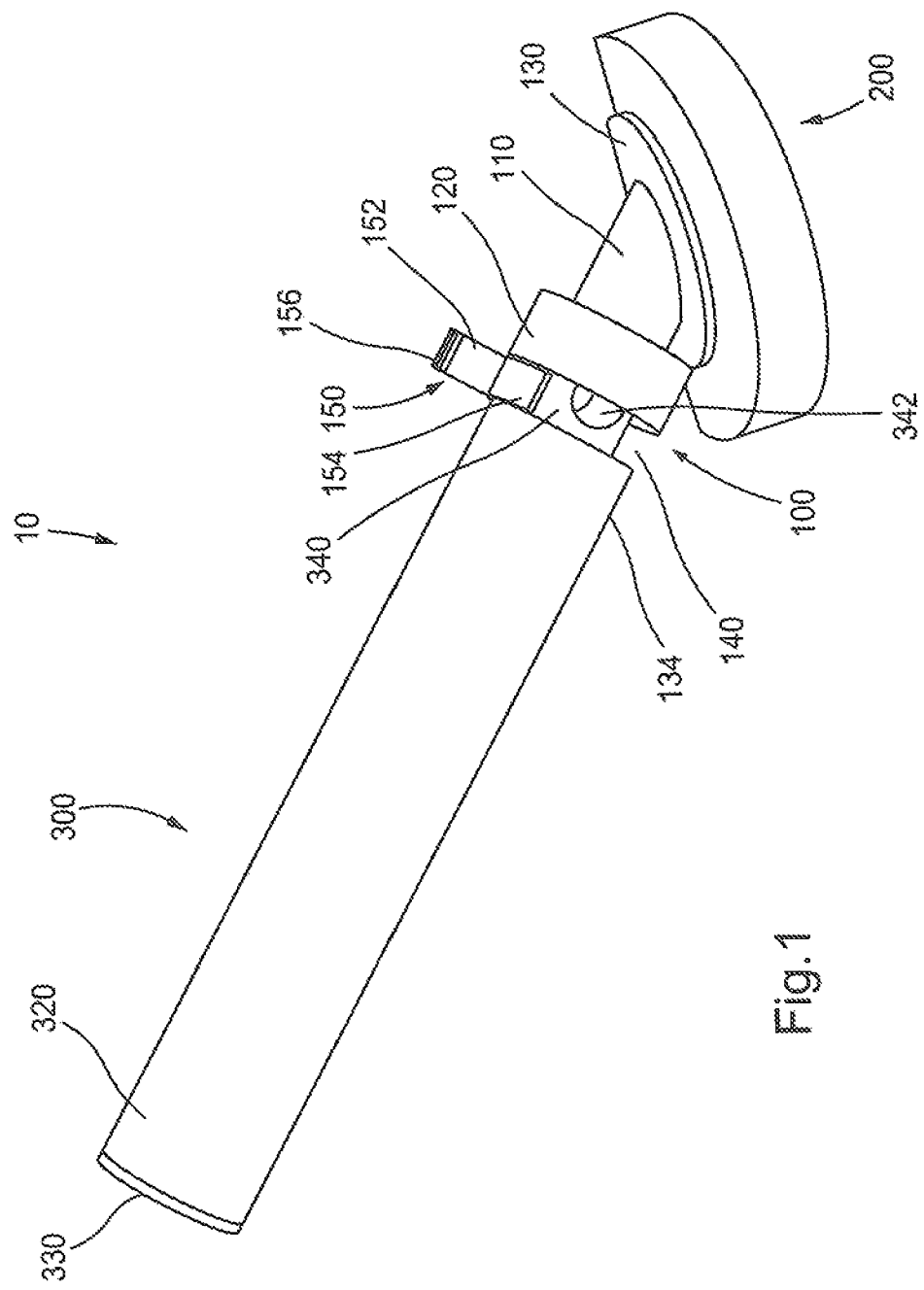
FIG. 1 is a perspective view of an antiseptic applicator, in accordance with certain aspects of the present invention.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Figure 2:
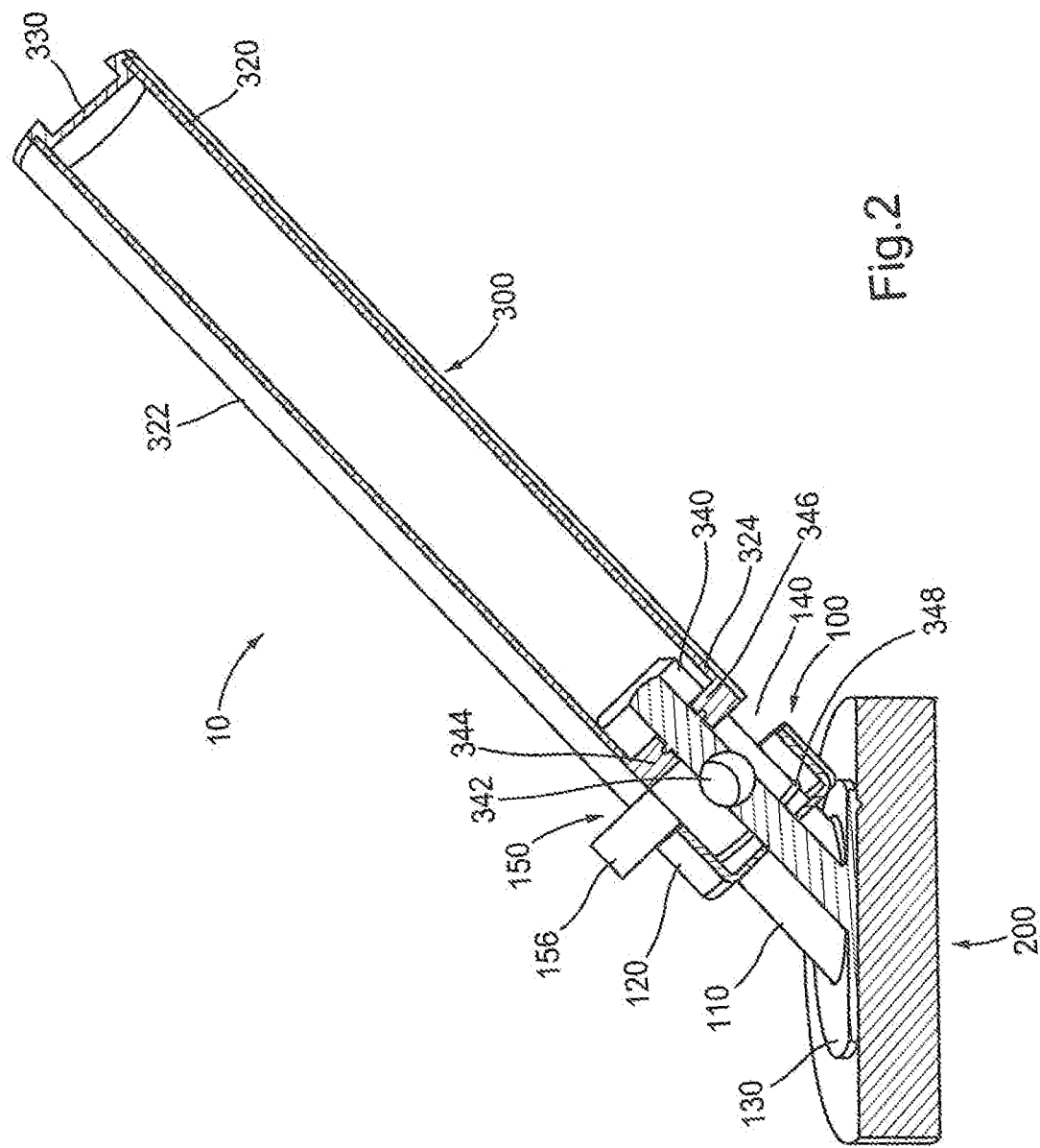
FIG. 2 is a side cutaway view of an antiseptic applicator, in accordance with certain aspects of the present invention.

The antiseptic applicator may be compact and ergonomically designed. As shown in FIGS. 1 and 2, an antiseptic applicator 10 may comprise a substantially hollow head portion 100, which may be cylindrical in shape, an application member 200 mounted to a distal end 110 of the head portion 100, and a solution container 300 slidably received by a proximal end 120 of the head portion 100. The solution container 300 may be cylindrical in shape to position concentrically into the head portion 100 with a proximal end 320 extending beyond the proximal end 120 of the head portion 100. The solution container may be formed with a grasping mechanism, such as an area of cross-hatching, for example, or a recessed area integrated into a side wall 322 of the container 300, to enhance the ability of a user to hold and/or push the solution container 300 in one direction with one hand, in order to translate the solution container 300 in an axial direction toward the distal end 110 of the head portion 100.

The application member 200 may be formed from a foam sponge material, for example, or any suitable material that allows the controlled application of the contained solution from the solution container 300 to a surface external to the applicator 10. The material chosen may be porous with a particular soak rate, for example, or may be provided with structural features, including slits or apertures, to direct and control the flow rate of the solution through the application member 200. The head portion 100 may be configured to have a mounting flange 130 at the distal end 110. The mounting flange 130 provides a surface for affixing the application member 200 to the head portion 100.

The solution container 300 is preferably a self-contained structure, formed of a suitable material, such as a plastic, e.g., a high-density polyethylene plastic, that is flexible, yet resistant to deformation and chemical leeching. The container 300 may be filled with various liquids such as antiseptics or medicaments, chemical compositions, cleansing agents, cosmetics, or the like, and preferably an antimicrobial liquid or gel composition, for antiseptic application to a patient prior to surgery. The container 300 is designed to withstand various heat and chemical sterilization techniques, which may be performed sequentially with a solution filling process, in accordance with techniques that are well known in the art, such as a blow-fill-seal technique. Preferable antimicrobial agents contained in the container include octenidine salts, chlorhexidine salts, alcohol, aldehyde, anilide, diamidine, halogen-releasing agent, silver compound, peroxygen, and/or phenols. A preferable octenidine salt includes octenidine dihydrochloride and a preferable chlorhexidine salt includes chlorhexidine gluconate.

As shown in FIG. 2, the container 300 may be an elongated cylinder formed by the sidewall 322. A closing member 330 may be provided at the proximal end 320 and a sealing plug 340 formed toward an insertion end 324 of the container 300 to seal shut an interior of the container 300. The plug 340 may be integrally formed with the distal end 110 of the head portion 100. The closing member 330 may be integrally formed with the container 300 or, for example, may be a separate component connected to the container, such as an end cap for mating via a threaded connection with the proximal end 320, or a plug that may be press fit or heat welded to the container 300, for sealing shut the open proximal end 320. Thus, in accordance with certain aspects of the present invention, with the sealing plug 340 in place, solution may be filled through the open proximal end 320 of the container 300 prior to the container 300 being sealed shut with the closing member 330.

The sealing plug 340 may be formed of a suitable material, such as a plastic, e.g., a high-density polyethylene plastic, having enough strength to effectively seal the insertion end 324 of the container 300 and prevent leaching of the contained solution. The sealing plug 340 may include one or more orifices 342 and a center configured such that the orifice 342 is in fluid communication with the distal end 110 of the head portion 100. As shown in FIG. 2, the sealing plug 340 may include a pair of diametrically opposing orifices.

As shown in FIGS. 1 and 2, the sealed container 300 having a solution contained therein may be slidably inserted into the proximal end 120 of the head portion 100. A retention mechanism (not shown), for example an annular retention ring, may be provided on the exterior of the side wall 322 toward the insertion end 324 of the container 300. The annular retention ring may cooperate with a first annular retention channel (not shown) configured into an interior of the head portion 100 to limit the axial movement of the container 300 in relation to the head portion 100 and to prevent the separation of the container 300 from the head portion 100 once joined in a final assembled position. This arrangement is shown in more detail in U.S. patent application Ser. No. 13/328,460, titled "Antiseptic Applicator," filed on Dec. 12, 2011, which is hereby incorporated by reference herein.

A mechanical stop 150 may be provided to secure the container 300 in the assembled position until the mechanical stop 150 is intentionally released prior to actuation of the applicator 10. In this manner, the orifice 342 in the sealing plug 340 is prevented from providing fluid communication between the container 300 and an interior fluid chamber of the head portion 100 during handling, storage and transport of the applicator 10. The mechanical stop 150 may be a hinged portion and preferably may be disposed toward with the proximal end 120 of the head portion 100 or toward the insertion end 324 of the container 300. A securing mechanism 152, such as a snap fit channel, for example, may be provided on an inner side of the mechanical stop to engage a first retention mechanism such as an annular retention ring (not shown) when the mechanical stop 150 is pressed against a circumferential surface portion 154 in a storage position. While only a portion of the surface portion 154 is shown in FIG. 2 for clarity, the surface portion 154 may extend all the way around the circumference of the head portion 100 or the container 300. Alternatively, the surface portion 154 may be removeably coupled to the insertion end 324 of the container 300 on one side and to the proximal end 120 of the head portion 100 on the other side. With the securing mechanism 152 thus engaged, the container 300 may be retarded from axial movement toward and away from the head portion 100 during assembly, handling or transport of the applicator 10. To disengage the mechanical stop 150, a user simply applies pressure against a release tab 156 to rotate the hinged stop 150 away from the circumferential surface portion 154 and disengage the securing mechanism 152. The release tab 156 may be angled to provide clearance between the stop 150 and the circumferential surface portion 154 when the stop 150 is hinged in a closed position with the securing mechanism 152 engaged. A user may thus easily disengage the stop 150 with one hand by applying pressure with one finger, such as a thumb, against the release tab 156 while holding the applicator 10.

In accordance with other aspects of the present invention, the mechanical stop 150 may be formed with a detent on an interior surface (not shown) to further prevent axial movement of the container 300 toward the head portion 100. The detent may extend into the interior portion of the head portion 100 or the container 300 near where the stop 150 is hinged and engage the insertion end 324 of the container 300 when in a closed position. Upon the rotational release of the stop 150 by pressure exerted against the release tab 156, the detent rotates along with the stop 150 and releases the insertion end 324 of the container to slide into the head portion 100. The stop 150 may be configured to lock into an open position once actuated.

As shown in FIG. 2, with the container 300 concentrically mounted in the head portion 100, as described above, and the application member 200 mounted to close off the distal end 110 of the head portion 100, the fluid chamber of the head portion 100 may be formed in the distal end of the head portion 100 between the application member 200 and the sealing plug 340. A fluid metering device, such as a pledget, for example, may be optionally provided in the fluid chamber to further control and/or direct the flow of solution from the container 300 when the assembly 10 is in use.

To activate the applicator 10 and release the solution from the container 300, a user may grasp the container 300 with one hand. The mechanical stop 150 may be disengaged by using a finger on the same hand to exert pressure against the release tab 156 and disengage the securing mechanism 152. The user may then pull the tab 156 along a circumferential direction. Because the circumferential portion 154 may be removeably coupled to the insertion end 324 of the container 300 and the proximal end 120 of the head portion 100, pulling the tab 156 will remove the tab 156 along with the circumferential portion 154 from apparatus 10, which can then be discarded. With the tab 156 and circumferential portion 154 removed, a gap 140 corresponding to of the circumferential portion 154 is present between the insertion end 324 of the container 300 and the proximal end 120 of the head portion 100. The container 300 is then free to be pushed forward toward the distal end of the head portion by closing the gap 140.

In another aspect of the present invention, instead of removing the tab 156 and the circumferential portion 154, when a retention ring is used, the user may either use their other hand to hold the head portion 100 and/or may press the head portion 100 against a stable surface while applying force against the container 300 to slide the container into the head portion 100. The application of the compressive force dislodges the retention ring from the first annular retention channel, allowing the container 300 to translate from a proximally disposed position further into the head portion 100. Continued applied force on the container 300 axially translates the container 300 toward the distal end of the head portion 100. This arrangement is shown in more detail in U.S. patent application Ser. No. 13/328,460, titled "Antiseptic Applicator," filed on Dec. 12, 2011, which is hereby incorporated by reference herein.

As shown in FIG. 2, the sealing plug 340 may be substantially cylindrically shaped and may extend from the proximal end 120 of the head portion 110 towards the distal end 324 of the container 300. The container 300 preferably includes a sealing ring 344 having a central opening (not shown), sized to tightly receive the sealing plug 340. The seal between the sealing plug 340 and the sealing ring 344 limits the fluid inside the container 300 from escaping into the head portion 100. As discussed above, the sealing plug 340 further comprises an orifice or a pair of diametrically opposed orifices 342 formed in a surface of the sealing plug. The inside of the sealing plug 340 may contain a hollow portion whereby the orifices 342 provide a path for fluid to flow from outside the sealing plug 340 to the inside of the sealing plug 340.

As the container 300 translates toward the distal end 110 of the head portion 100, the container 300, preferably including the sealing ring 344, slides to overlap the orifices 342. Once a rear portion 346 of the sealing ring 344 passes over the orifices 342. The fluid in the container 300 is no longer restricted and may flow into the hollow portion of the sealing plug 340 via the orifices 342. The outer diameter of the container 300 may be slightly smaller than the inner diameter of the proximal end 120 of the head portion 100 so during translation, the container may slide within the proximal end 120 of the head portion 100. Alternatively, the inner diameter of the container 300 may be slightly larger than the outer diameter of the proximal end 120 of the head portion 100 so during translation, the proximal end 120 may slide within the insertion end 324 of the container 300. As the container is further translated toward the head portion 100, a larger area of the orifices 342 is exposed. The more area of the orifices that are exposed, more fluid will travel from the container 300 into the sealing plug 340. Thus, an operator may control the amount of fluid that is dispensed by increasing or decreasing the translation of the container 300.

The sealing plug 340, by virtue of containing a hollow portion, may form a fluid channel through the interior portion of the sealing plug 340. Additional orifices provided near the end of the sealing plug 340 allows fluid to be communicated from the hollow portion of the sealing plug 340, directly into the fluid chamber in the distal end 110 of the head portion 100. By controlling the translation of the container 300, the solution may soak into, or otherwise flow through, the application material 200 at a specified volume and rate. The fluid chamber may serve to accumulate and distribute the solution evenly over substantially the entire area of the application material 200. Once the application material 200 is engorged, for example, the solution may then be applied to a patient by wiping the distal surface of the application material 200 against the skin.

According to another aspect of the present invention, a second retention mechanism such as an annular retention ring may be provided in the applicator 10. As shown in FIG. 2, the second retention mechanism 348 may be provided on a surface of the plug 340 and disposed between the orifices and the distal end of the head portion. A portion of the container 300, for example, the sealing ring 344, may thus engage the second retention mechanism after a predetermined distance of translation into the head portion 100 to substantially secure the container 300 and maintain the applicator 10 in an open position. Thus, the second retention mechanism 348 prevents further translation of the container 300 once the insertion end 324 of the container 300 contacts the second retention mechanism 348. Alternatively, the second retention mechanism may be provided along the interior of the head portion 100 that is disposed closer toward the distal end 110 than the first retention mechanism. This alternate arrangement is shown and described in more detail in U.S. patent application Ser. No. 13/328,460, titled "Antiseptic Applicator," filed on Dec. 12, 2011, which is hereby incorporated by reference herein.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
   a head portion having a proximal end, a distal end, and an interior portion defining a fluid chamber;
   a container comprising a sealing ring, wherein the container is slidably coupled to the head portion;
   plug sealing an end of and extending into the container prior to actuation of the container,
   a foam application member attached to the distal end; and
   one or more orifices formed through a surface of the plug, and
   wherein an interior of the container is placed in fluid communication with the application member by way of a fluid conduit that is formed through the plug from the container to the fluid chamber when the container is actuated into the proximal end of the head portion to bring an area of the one or more orifices into fluid communication with the container by moving the sealing ring relative to the plug,
   wherein the container is configured to translate relative to the head portion during use such that the area of the one or more orifices is variable during use.

2. The applicator assembly of claim 1, further comprising a mechanical stop to secure the container in a predetermined position until the stop is released prior to actuation of the container.

3. The applicatory assembly of claim 2, wherein the actuation of the container comprises axial translation.

4. The applicator assembly of claim 2, wherein the mechanical stop comprises a hinged portion disposed toward the proximal end of the head portion or toward an insertion end of the container.

5. The applicator assembly of claim 4, wherein the mechanical stop further comprises a securing mechanism to retard axial translation of the container.

6. The applicator assembly of claim 5, wherein the securing mechanism comprises a snap fit channel for engaging a first retention mechanism on an exterior of the container to secure the applicator assembly in a storage position.

7. The applicator assembly of claim 2, wherein the mechanical stop comprises a circumferentially extending surface portion connected to the proximal end of the head portion and a distal end of the container.

8. The application assembly of claim 7, wherein the circumferentially extending surface portion is disposed within a gap between the proximal end of the head portion and the distal end of the container.

9. The applicator assembly of claim 1, wherein the plug comprises a hollow body portion.

10. The applicator assembly of claim 9, wherein one or more orifices provide fluid communication from an exterior portion of the plug into the hollow body portion when the container translates toward the distal end of the head portion.

11. The applicator assembly of claim 1, further comprising a second retention mechanism provided on a surface of the plug, wherein the second retention mechanism retards axial translation of the container.

12. The applicator assembly of claim 11, wherein the second retention mechanism is disposed between the one or more orifices and the distal end of the head portion.

13. The applicator assembly of claim 1, wherein the plug extends axially within the container.

14. The applicator assembly of claim 1, wherein the sealing ring prevents fluid communication between the container and the one or more orifices before the container translates towards the distal end of the head portion.

15. The applicator assembly of claim 1, wherein the one or more orifices comprises a pair of orifices opposing each other.

16. The applicator assembly of claim 1, wherein the plug is integrally formed with the distal end of the head portion.

17. The applicator assembly of claim 11, wherein the second retention mechanism comprises an annular retention ring.

18. The applicator assembly of claim 1, wherein the foam application member has a perimeter larger than a perimeter of the distal end of the container.

19. The applicator assembly of claim 1, further comprising a mounting flange at the distal end of the container, wherein the foam application member is affixed to the mounting flange, and wherein the application member has a perimeter larger than the perimeter of the mounting flange.

20. The applicator assembly of claim 1, wherein the foam application member comprises a porous material having a soak rate sufficient to distribute solution through the application member.

21. The applicator assembly of claim 1, wherein the container comprises an antiseptic solution.

22. The applicator assembly of claim 21, wherein the antiseptic solution comprises an antimicrobial agent selected from the group consisting of octenidine salts, chlorhexidine salts, alcohols, aldehydes, anilides, diamidines, halogen-releasing agents, sliver compounds, peroxygens, and phenols.

23. The applicator assembly of claim 22, wherein the antiseptic solution comprises an octenidine salt or a chlorhexidine salt.

* * * * *